United States Patent
Hillis

(10) Patent No.: US 9,671,350 B2
(45) Date of Patent: Jun. 6, 2017

(54) TEST MASS COMPENSATION OF MASS MEASUREMENT DRIFT IN A MICROCANTILEVER RESONATOR

(71) Applicant: APPLIED INVENTION, LLC, Burbank, CA (US)

(72) Inventor: W. Daniel Hillis, Encino, CA (US)

(73) Assignee: Applied Invention, LLC, Glendale, CA (US)

(*) Notice: Subject to any disclaimer, the term of this patent is extended or adjusted under 35 U.S.C. 154(b) by 168 days.

(21) Appl. No.: 14/477,287

(22) Filed: Sep. 4, 2014

(65) Prior Publication Data

US 2015/0064803 A1  Mar. 5, 2015

Related U.S. Application Data

(60) Provisional application No. 61/873,772, filed on Sep. 4, 2013.

(51) Int. Cl.
| | | |
|---|---|---|
| *G01N 33/48* | (2006.01) | |
| *G01N 33/50* | (2006.01) | |
| *G01N 21/84* | (2006.01) | |
| *G01Q 10/04* | (2010.01) | |
| *G02B 6/36* | (2006.01) | |
| *G01N 29/02* | (2006.01) | |
| *G01N 5/02* | (2006.01) | |
| *G01N 29/30* | (2006.01) | |

(Continued)

(52) U.S. Cl.
CPC .............. *G01N 21/84* (2013.01); *G01N 5/02* (2013.01); *G01N 29/022* (2013.01); *G01N 29/30* (2013.01); *G01Q 10/045* (2013.01); *G02B 6/3656* (2013.01); *G06F 19/70* (2013.01); *G01N 9/002* (2013.01); *G01N 2015/0065* (2013.01); *G01N 2015/1087* (2013.01); *G01N 2291/0256* (2013.01); *G01N 2291/0427* (2013.01)

(58) Field of Classification Search
None
See application file for complete search history.

(56) References Cited

U.S. PATENT DOCUMENTS

| | | | |
|---|---|---|---|
| 5,719,324 A * | 2/1998 | Thundat ............... | G01N 29/022 73/24.01 |
| 2006/0191320 A1* | 8/2006 | Pinnaduwage ...... | G01N 29/022 73/24.06 |
| 2007/0141721 A1* | 6/2007 | Vafai ................. | G01N 33/54373 436/518 |

OTHER PUBLICATIONS

Burg et al. Weighing of Biomolecules, Single Cells and Single Nanoparticles in Fluid. Nature vol. 446 (2007); pp. 1066-1069 doi:10.1038/nature05741.

* cited by examiner

*Primary Examiner* — Russell S Negin
(74) *Attorney, Agent, or Firm* — Michael A. Glenn; Perkins Coie LLP

(57) ABSTRACT

The present disclosure provides methods and mechanisms for measuring small masses attached to a substrate within a microcantilever. Specifically, the disclosure describes the measurement of small particles accumulated at a substrate that cannot be flowed through a microchannel within a microcantilever. A resonance measurement is acquired at a first time. A pair resonance measurements is then acquired at a second point in time—one with the test mass at a first position off or along the microcantilever, the second with the test mass at a second position along the microcantilever. Comparing the resonance frequencies determined for the two test mass positions allows for disambiguation of (Continued)

changes in the mass of the particles from changes in the resonant behavior of the microcantilever itself.

34 Claims, 4 Drawing Sheets

(51) Int. Cl.
*G06F 19/00* (2011.01)
*G01N 15/10* (2006.01)
*G01N 15/00* (2006.01)
*G01N 9/00* (2006.01)

TEST MASS COMPENSATION OF MASS MEASUREMENT DRIFT IN A MICROCANTILEVER RESONATOR

CROSS-REFERENCE TO RELATED APPLICATION(S) AND PRIORITY DATE

This application is entitled to the benefit of and/or the right of priority to U.S. Provisional Application No. 61/873,772, entitled "TEST MASS COMPENSATION OF MASS MEASUREMENT DRIFT IN A MICROCANTILEVER RESONATOR", filed Sep. 4, 2013, which is hereby incorporated by reference in its entirety for all purposes. This application is therefore entitled to a priority date of Sep. 4, 2013.

TECHNICAL FIELD

The invention relates to resonance-based measurement of very small masses using a microcantilever, and in particular the measurement of very small particles accumulated at a substrate on the microcantilever.

BACKGROUND

Microcantilevers containing a microchannel can enable precise resonance-based measurement of very small masses entrained in a fluid flowing through the microchannel. Burg et al. describe one such system based on the principle that "the resonance frequency of a suspended microfluidic channel . . . is highly sensitive to the presence of molecules or particles whose mass density differs from that of the [fluid]." (Burg, Thomas P.; Godin, Michel; Knudsen, Scott M.; Shen, Wenjiang; Carlson, Greg; Foster, John S.; Babcock, Ken; Manalis, Scott R. "Weighing of biomolecules, single cells and single nanoparticles in fluid," Nature, 446, 1066-1069 (Apr. 26, 2007)).

FIG. 1A shows a schematic representation 100a of a microcantilever 110 with a microchannel 120 according to the prior art. A thin (e.g., with thickness O[μm]) silicon microcantilever 110 extends outward from an essentially rigid base 130 into a cavity 190. As illustrated by the arrows indicating the direction of flow, a U-shaped microchannel 120 (e.g., with thickness and depth O[μm]) etched in the silicon transports a fluid outward from the rigid base 130 and into the body of the microcantilever 110 before returning the fluid to the rigid base 130. The free end 140 of the microcantilever 110 readily flexes in and out of the plane of FIG. 1A. Using an electrostatic drive electrode (not shown) driven by a gain controlled oscillator circuit, it is possible to excite the microcantilever 110 within a vacuum cavity to determine its characteristic resonance frequency.

FIG. 19 shows an isometric view 100b of a microcantilever 110 as schematically represented in FIG. 1a. FIG. 1B is provided to illustrate how a microcantilever 110 may be configured to extend outward from a rigid base 130 into a cavity 190.

FIG. 1C shows a first technique 100c for measuring small masses using a microcantilever 110 with a microchannel 120 according to the prior art. In this approach, the resonance frequency of the microcantilever 110 is monitored continuously as fluid flowing through the microchannel 120 conveys discrete sample particles 150a-c toward and away from the tip 140 of the microcantilever 110. Provided that the concentration of the particles 150a-c within the fluid is relatively sparse (i.e. it is relatively unlikely that two particles will simultaneously flow along the length of microchannel 120 within the microcantilever 110), the resonance frequency will vary according to the following equation:

$$f = \frac{1}{2\pi}\sqrt{\frac{k}{\overline{m} + \alpha m}} \qquad \text{Equation (1)}$$

where k is the spring constant of the microcantilever 110, $\overline{m}$ is the effective mass of the microcantilever 110 and any fluid therein, in is the mass of an individual sample particle 150a-c, and a is a geometric constant reflecting the current location of the sample particle 150a-c. When an individual particle 150a-c is near the tip 140 of the microcantilever 110, α≈1. When an individual particle 150a-c is near the rigid base 130 of the microcantilever 110 (or when no particles are within the length of the microchannel 120 within the microcantilever 110), α≈0. Thus, by observing the peak-to-trough differences in the resonance frequency as it varies over time, it is possible to determine the mass of an individual sample particle 150a-c as it flows past the tip 140 of the microcantilever 110.

FIG. 1D shows a second technique 100d for measuring small masses using a microcantilever 110 with a microchannel 120 according to the prior art. In this approach, an agent 160 that will bind the sample particles is immobilized against the interior walls of the microchannel prior to testing. Fluid containing sample particles is then flowed through the microchannel 120 and a single layer of sample particles adheres to the binding agent 160. A subsequent resonance measurement allows the mass of the layer of sample particles to be determined from Equation 1. However, in this approach, $\overline{m}$ includes the mass of the binding agent 160, and a value of α≈0.25 reflects the approximately uniform distribution of the sample particle layer along the length of the microcantilever 110.

The above two approaches do provide high measurement sensitivity, resolving masses as small as $300\times10^{-18}$ g. However, both approaches are only applicable to sample particles that can be conveyed by the fluid flowing through the microchannel. The above two approaches are thus not well suited, for example, to measurement of biological particles that must be grown on a mechanical substrate that is too large or too fragile to be conveyed through the microchannel.

SUMMARY

Embodiments of the present disclosure describe methods, systems, and apparatus for determining the mass of small particles using a microcantilever with an associated substrate. According to some embodiments, small particles may accumulate or are grown or reproduce on a substrate on a microcantilever. In order to determine the change in mass of the accumulated small particles, the microcantilever is excited and a resonance frequency is measured at a first and a second time, the resonance frequency of the microcantilever being a function of the mass of the accumulated biological particles. According to some embodiments, in order to correct for drift in the resonance behavior of the microcantilever over time, a test mass is introduced that may be actuated between two positions either off board or onboard the microcantilever. In such embodiments, two resonance frequencies are measured at the second time. Once with the test mass at a first position and once with the test mass at the second position. By taking two measurements of the resonance frequency of the microcantilever at the second time (with the test mass in two different positions) the drift in resonance behavior of the microcantilever caused by the additional mass of the biological particles may be accounted for.

BRIEF DESCRIPTION OF THE DRAWINGS

The present embodiments are illustrated by way of example and are not intended to be limited by the figures of the accompanying drawings. In the drawings.

DETAILED DESCRIPTION

From the foregoing, it will be appreciated that specific embodiments of the invention have been described herein for purposes of illustration, but that various modifications may be made without deviating from the scope of the invention. Accordingly, the invention is not limited except as by the appended claims.

The present teachings provide for methods and mechanisms for measuring small masses attached to a substrate within a microcantilever. Specifically, the teachings allows for measurement of particles accumulated, grown, or reproduced at a substrate that cannot be flowed through a microchannel within a microcantilever. While the present disclosure describes various embodiments in the context of grown or reproduced small biological particles, it shall be understood that this is done for illustrative purposes, and that the present teachings may be applied to the measurement of changes in mass of any types of small particles where those changes occur in situ, for example in the area of nanotechnology.

Figure 1A:
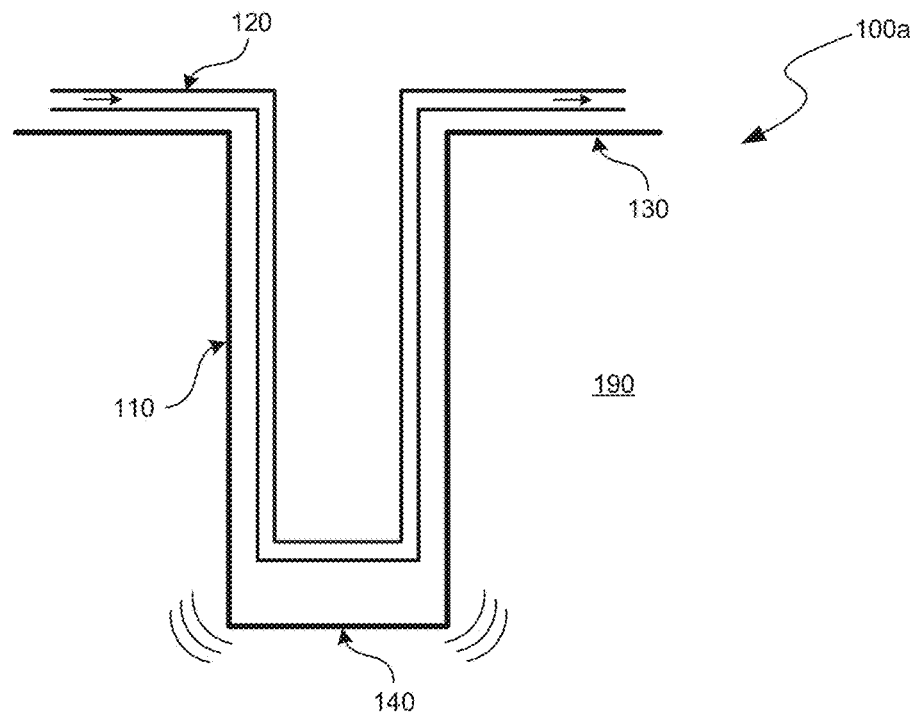
FIG. 1A shows a schematic representation of a microcantilever with a microchannel according to the prior art.
Figure 1B:
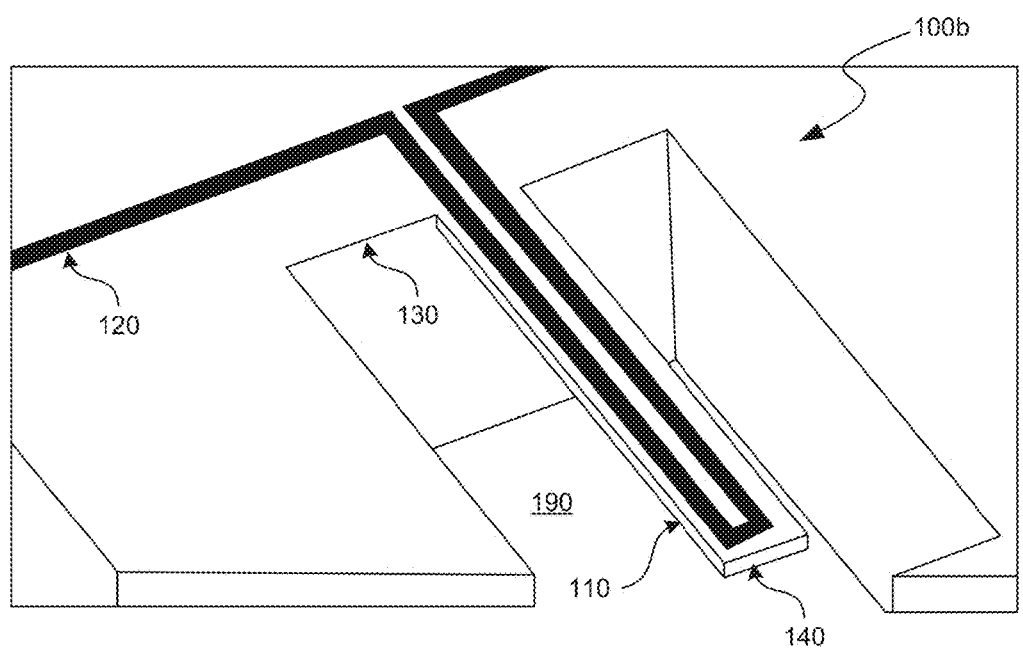
FIG. 1B shows an isometric view of a microcantilever according to the prior art.
Figure 1C:
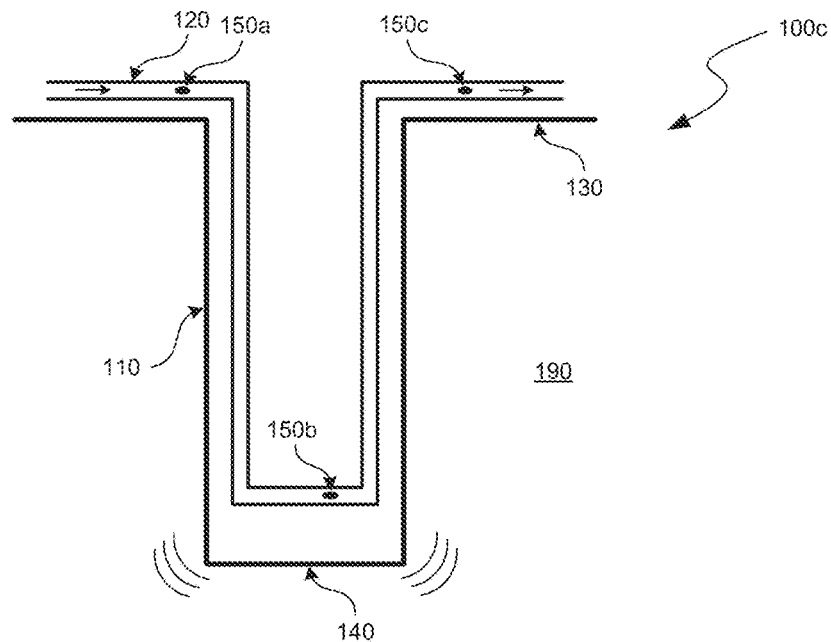
FIG. 1C shows a first technique for measuring small masses using a microcantilever with a microchannel according to the prior art.
Figure 1D:
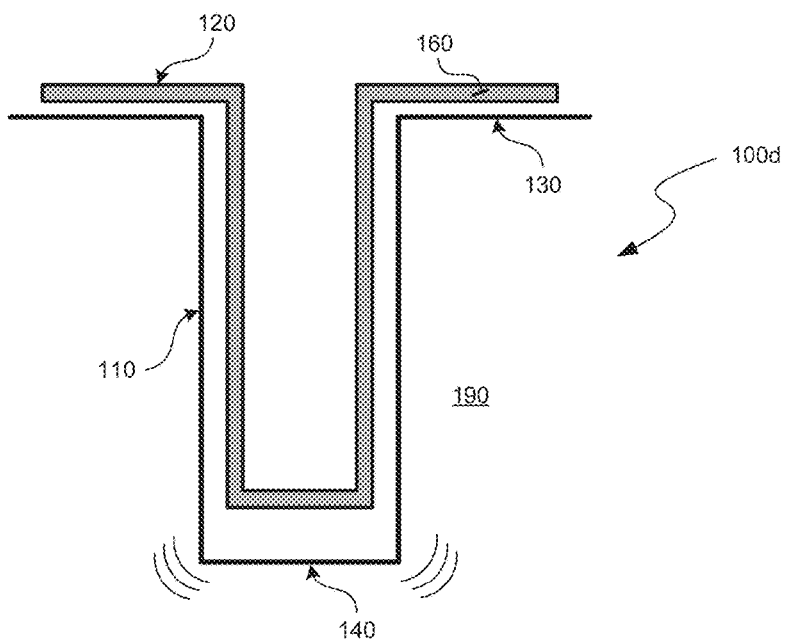
FIG. 1D shows a second technique for measuring small masses using a microcantilever with a microchannel according to the prior art.
Figure 2:
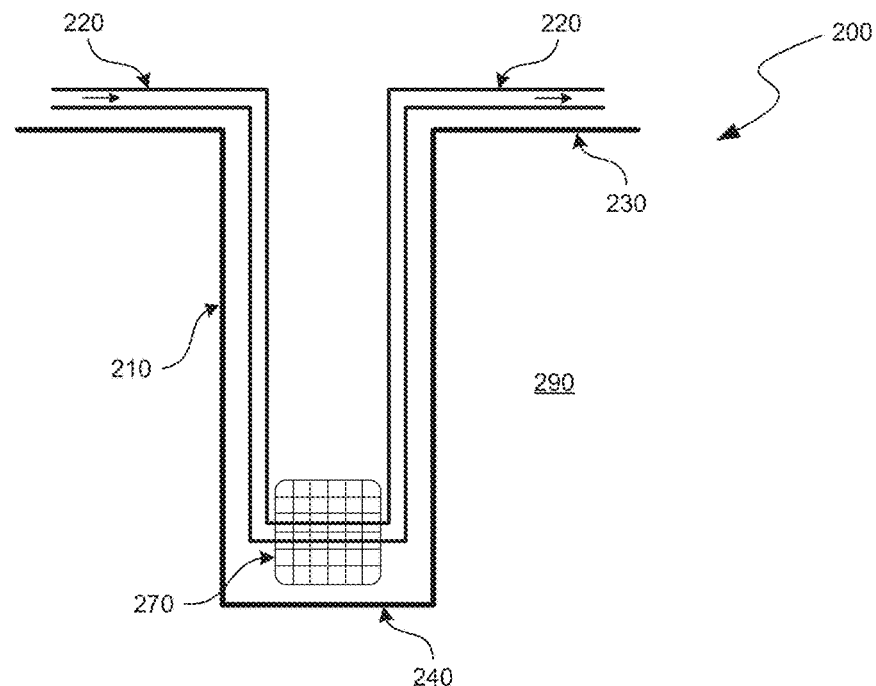
FIG. 2 shows a schematic representation of an example microcantilever incorporating a substrate according to some embodiments of the present disclosure.

FIG. 2 shows a schematic representation of a microcantilever 210 incorporating a substrate 270 according to some embodiments of the present disclosure. Similar to microcantilever 110 described in FIGS. 1A-1D, microcantilever 210 may comprise a thin (e.g., with thickness O[μm]) body having a free end 240 and a rigid end connected to a rigid base 230 and extending outward into a cavity 290. Formed at least partially on or within microcantilever 210, a microchannel 220 (e.g. with width and depth O[μm]) may be configured to transport fluid (e.g. water) along the body of the microcantilever from the rigid based 230 to the free end 240 and back to the rigid base 230. In some embodiments, the microchannel 220 may be configured to transport sample particles and/or food to substrate 270 in order to seed and/or support growth and reproduction of particles accumulating at the substrate 270. According to some embodiments, the microchannel 220 may be configured to transport waste produced by the particles away from the substrate 270.

According to some embodiments, microcantilever 210 with microchannel 220 may be fabricated by creating buried channels in silicon-on-insulator wafers and then dry etching the wafer to form the microchannel within the microcantilever. A person having skill in the art will recognize that other materials and fabrication processes may be suitable to use while remaining within the scope of the present teachings. As a non-limiting example for illustrative purposes, a microcantilever 210 may be approximately 200 μm long (i.e., from rigid base 230 to free end 240) 50 μm wide and 10 μm thick with a microchannel 220 of approximately 10 μm wide and 3 μm deep, according to some embodiments. A person having skill in the art will recognize that different dimensions may be suitable depending on a number of factors, including the size of the sample particles to be measured.

Using a means for exciting microcantilever 210, for example via an electrostatic drive electrode (not shown) driven by a gain controlled oscillator circuit (not shown), microcantilever 210, may be caused to vibrate within cavity 290. The resulting vibrations of microcantilever 210 may then be measured and a resonance frequency determined using a fight source and optical sensor, for example a laser pointed substantially at the free end 240 of the microcantilever 210, wherein the reflected light from the laser is picked up by a position sensitive photo detector.

The cavity 290, within which the microcantilever 210 is located, may be filed with gas (e.g. air) or fluid (e.g. water), however, due to the damping effect of the surrounding material within cavity 290, a microcantilever resonator within a gas (e.g. air) filed cavity will have a higher quality factor (i.e. exhibit less energy loss due to damping) than fluid (e.g. water) filed cavity (assuming equal dimensions of the microcantilever in each instance). A higher quality factor may result in reduced phase noise leading to more accurate determinations of the resonance frequency due to the higher stability of the measured frequency. According to some embodiments, in order to maximize the quality factor of a given microcantilever resonator, microcantilever 210 may be surrounded by a vacuum enclosed by cavity 290.

The substrate 270 may provide mechanical support to the sample particles (not shown) that are to be measured. In other words, substrate 270 may be configured to support the accumulation, growth and/or reproduction of the particles to be measured. Generally, the substrate 270 may be formed within or upon the microcantilever 210 using micromechanical etching and deposition techniques (e.g. bulk micromachining and surface micromachining) well known in the art. For example, according to some embodiments, the substrate 270 may comprise a lattice, mesh, or set of linear notches within a chamber located along the etched microchannel 220. As described earlier, according to some embodiments, a fluid (e.g. water) may flow through the microchannel 220, conveying food to and removing waste from the biological particles (e.g. bacteria) growing or reproducing on the substrate 270. An example substrate 270 is schematically shown in FIG. 2 located substantially near the free end 240 of microcantilever 210, however it shall be understood that this is a non-limiting example. Substrate 270 may include one or more individual substrates of varying geometry located anywhere along (on or within) the body of microcantilever 210, wherein the configuration is accounted for in the geometric parameter $\alpha_s$ as referenced below in Equation 4.

To measure changes in the mass of the biological particles on the substrate 270, resonance measurements can be made at two different points in time. However, as noted above, simply determining two resonance frequencies according to Equation 1 at widely separated times, namely $$f_1 = \frac{1}{2\pi}\sqrt{\frac{k_1}{\overline{m} + \alpha m_1}} \qquad \text{Equation (2)}$$

$$f_2 = \frac{1}{2\pi}\sqrt{\frac{k_2}{\overline{m} + \alpha m_2}} \qquad \text{Equation (3)}$$

in some cases may not suffice because it is possible for the resonance behavior of the microcantilever 210 to drift over time. That is, $m_1$ may be determined using Equation 2 as described for Equation 1, but $m_2$ may in some cases not be reliably calculated because it is possible that $k_2 \neq k_1$.

To address this difficulty, according to some embodiments, a test mass may be introduced that may be actuated between two positions a and b. The mass of the test mass is known with a high degree of accuracy. According to some embodiments, position b may be onboard the microcantilever, so that the test mass moves with the microcantilever as it flexes, and is known with a high degree of accuracy. Position a may either be onboard or offboard the microcantilever; if onboard the microcantilever, position a may also be known with a high degree of accuracy.

A resonance measurement may be made at a first time, generally as described for Equation 1, to determine the mass of the biological particles at the first time. More specifically, $m_1$ is determined from the following equation:

$$f_1 = \frac{1}{2\pi}\sqrt{\frac{k_1}{\overline{m} + \alpha_s m_1}} \qquad \text{Equation (4)}$$

Here, $\overline{m}$ is the effective mass of the microcantilever, the substrate, and any fluid therein; and $\alpha_s$ is a geometric parameter reflecting the distribution of the biological particles along the length of the microcantilever (i.e. the location and lengthwise extent of the substrate).

A pair of resonance measurements may be made at second time—one with the test mass at position a and one with test mass at position b. As indicated by the following equations:

$$f_2^a = \frac{1}{2\pi}\sqrt{\frac{k_2}{\overline{m} + \alpha_s m_2 + \alpha_t^a m_t}} \qquad \text{Equation (5)}$$

$$f_2^b = \frac{1}{2\pi}\sqrt{\frac{k_2}{\overline{m} + \alpha_s m_2 + \alpha_t^b m_t}} \qquad \text{Equation (6)}$$

As noted above, the mass of the test mass and the locations of the two positions a (if onboard the microcantilever) and b are known with a high degree of accuracy. Thus $m_t$, $\alpha_t^a$, and $\alpha_t^b$ are known and Equations 5 and 6 can be solved for the two unknowns $k_2$ and $m_2$. Comparing $m_2$ $m_1$ allows the change in the mass of the biological particles to be determined.

It should be noted that the test mass can also be used to perform an initial calibration of the microcantilever with an empty substrate. At a time before any biological particles have grown on the substrate, a pair of resonance measurements is made.

$$f_0^a = \frac{1}{2\pi}\sqrt{\frac{k_0}{\overline{m} + \alpha_s m_0 + \alpha_t^a m_t}} \qquad \text{Equation (7)}$$

$$f_0^b = \frac{1}{2\pi}\sqrt{\frac{k_0}{\overline{m} + \alpha_s m_0 + \alpha_t^b m_t}} \qquad \text{Equation (8)}$$

Because $m_0 \equiv 0$, Equations 7 and 8 can be solved for $k_0$ and, more significantly, $\overline{m}$. The test mass can thus aid in characterizing the effective mass of the microcantilever, substrate, and any fluid therein.

Figure 3:
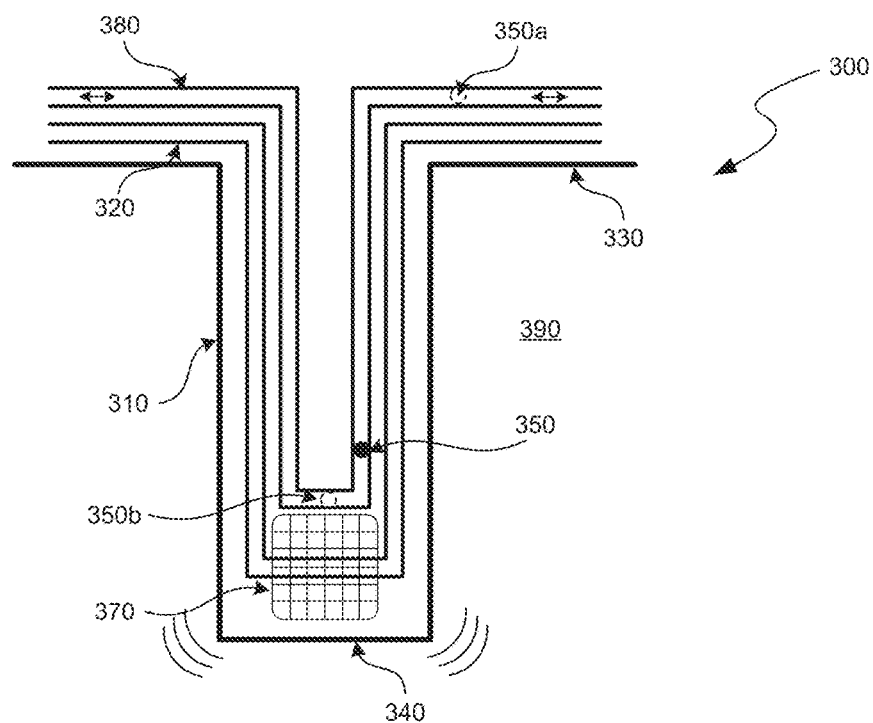
FIG. 3 shows a first example technique for measuring small masses using a microcantilever and a microchannel based test mass, according to some embodiments of the present disclosure.

FIG. 3 shows a first technique 300 for measuring small masses using a microcantilever 310 with a microchannel 320, substrate 370, and a microchannel-based test mass 350, according to some embodiments of the present disclosure. According to some embodiments, the test mass 350 may be actuated fluidically in a manner similar to the movement of the sample particles along the microchannel 220 in FIG. 2. As shown in FIG. 3, a separate test mass microchannel 380 interior to the feed and waste microchannel 320 may allow the test mass 350 to be conveyed by a precise switchable flow between predetermined positions 350a and 350b. As previously described position 350b may be on the microcantilever 310 (e.g. substantially near fee end 340) and position 350a may either be on the microcantilever 310 or offboard the microcantilever 310 and within the rigid base 330. Note that in FIG. 3, position 350a is shown offboard the microcantilever 310, and thus need not be known with great precision. Despite slight possible variations in position 350a, in such a configuration, $\alpha_t^a \equiv 0$.

Figure 4:
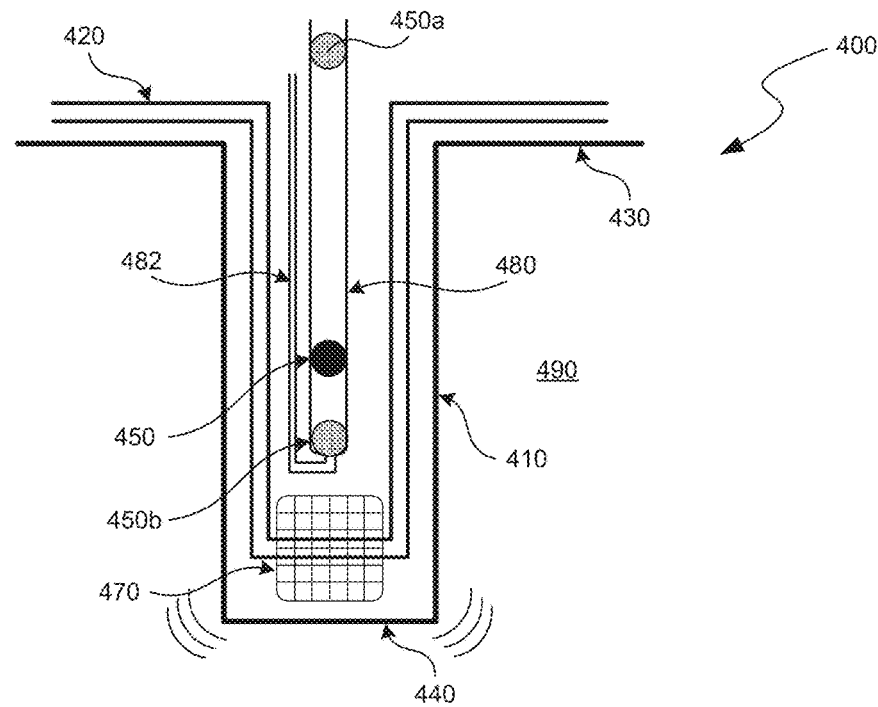
FIG. 4 shows a second example technique for measuring small masses using a microcantilever and a sliding test mass, according to some embodiments of the present disclosure.

FIG. 4 shows a second technique 400 for measuring small masses using a microcantilever 410 with a microchannel 420, a substrate 470, and a sliding test mass 450, according to some embodiments of the present disclosure. In some embodiments, pressure and suction may be used to actuate the test mass 450 to and from positions 450a and 450b within a test mass chamber 480 that extends outward from the rigid base 430 onto the microcantilever 410 towards the free end 440. According to some embodiments, a lossy (e.g. thin) return line 482 may vent to atmosphere or a fluid reservoir (i.e. outside the vacuum cavity 490) and may allow gas (e.g. air) fluid (e.g. water) to flow into the region of the test mass chamber 480 between the test mass 450 and the distal end of the test mass chamber 480. Alternatively, according to some embodiments, the test mass chamber 480 may be evacuated and the test mass 450 magnetically actuated to either end of the chamber 480. Note that in FIG. 4, as in FIG. 3, position 450a is shown as being offboard the microcantilever 410, and therefore $\alpha_t^a \equiv 0$.

Figure 5:
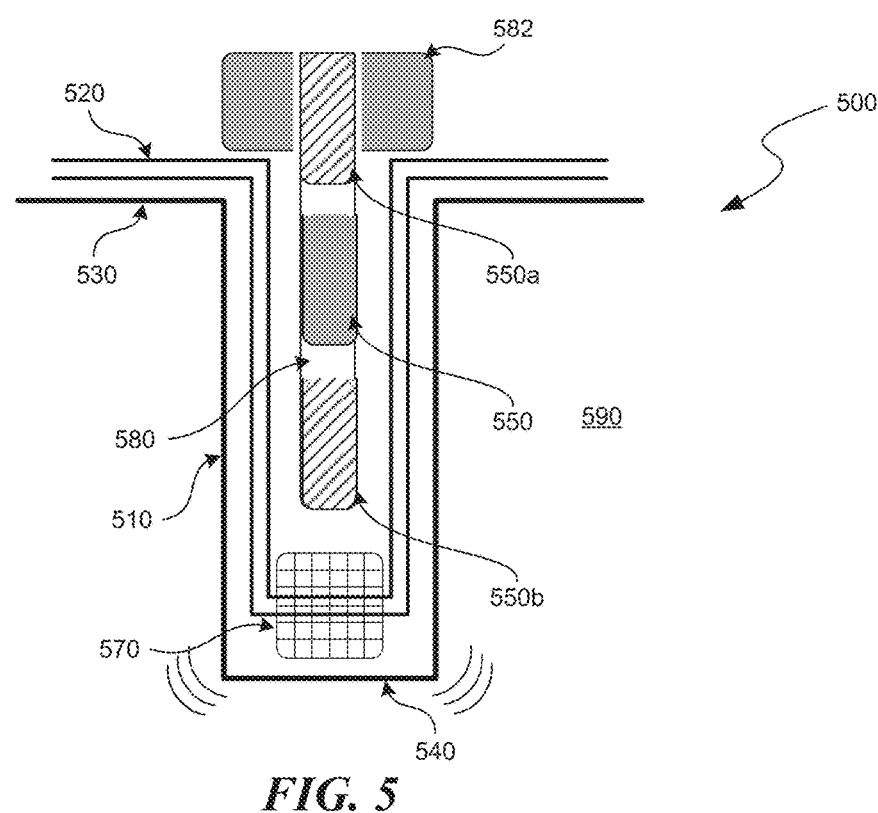
FIG. 5 shows a third example technique for measuring small masses using a microcantilever and a linearly actuated test mass according to some embodiments of the present disclosure.

FIG. 5 shows a third technique 500 for measuring small masses using a microcantilever 510 with a microchannel 520, substrate 570, and a linearly actuated test mass 550, according to some embodiments of the present disclosure. In such embodiments, an actuator 582 may slide an oblong test mass 550 from position 550a outward to position 550b along a path 580 that extends outward from rigid base 530 onto the microcantilever 510 towards the free end 540. According to some embodiments, actuator 582 may be a micromechanical actuator such as an electrostatic linear stepper motor fabricated using micro-machining techniques well known in the art. (See e.g., Tas, N. R.; Sonnenberg, A. H.; Sander, A. F M; Elwenspoek, M. C., "Surface Micromachined Linear Electrostatic Stepper Motor", Micro Electro Mechanical Systems, 1997. MEMS '97, Proceedings, IEEE, Tenth Annual International Workshop, pp. 215-220, 26-30 Jan. 1997.) The test mass 550, coupled to the shuttle of the actuator 582 (e.g., stepper motor), may slide along the path 582. For example, path 582 may be a track, in a slot, or under a cover that ensures that the test mass 550 moves with the microcantilever 510 as it flexes. Note that in FIG. 5, as in FIGS. 3 and 4, the test mass 550 is entirely offboard the microcantilever 510 when in position 550*a*, therefore $\alpha_t^a \equiv 0$. In a variation of the system illustrated in FIG. 5, an actuator 582 may be a rotary motor that moves the test mass 550 between positions 550*a* and 550*b* in an oscillatory fashion, wherein the pair of measurements described by Equations 5 and 6 are obtained in a periodic fashion.

Disclaimers

The above detailed description of embodiments of the disclosure is not intended to be exhaustive or to limit the teachings to the precise form disclosed above. While specific embodiments of, and examples for, the disclosure are described above for illustrative purposes, various equivalent modifications are possible within the scope of the disclosure, as those skilled in the relevant art will recognize. The scope of the invention is limited only by the claims.

Reference in this specification to "one embodiment", "an embodiment", or "some embodiments" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed above in more detail, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

While some aspects of the disclosure may be presented herein in some claim forms, the inventors contemplate the various aspects of the disclosure in any number of claim forms. For example, while only one aspect of the disclosure is recited as a means-plus-function claim under 35 U.S.C. §112(f), other aspects can likewise be embodied as a means-plus-function claim, or in other forms. (Any claims intended to be treated under 35 U.S.C. §112(f) will begin with the words "means for".) Accordingly, the applicant reserves the right to add additional claims after filing the application to pursue such additional claim forms for other aspects of the disclosure.

What is claimed is:

1. A method for determining the change in mass of particles accumulated on a substrate of a microcantilever, the method comprising:
    determining a first mass of the particles at a first time based on a measured first resonance frequency of the microcantilever;
    determining a second mass of the particles at a second time based on a measured second resonance frequency of the microcantilever, wherein determining the second mass of the particles at the second time includes:
        measuring the second resonance frequency of the microcantilever when a known test mass is at a first position; and
        measuring the second resonance frequency of the microcantilever when the known test mass is at a second position;
        wherein the known test mass is configured to be actuated between the first position and the second position; and
    determining a change in mass of the particles based on the first mass and the second mass.

2. The method of claim 1 wherein, the first mass is determined based on the first resonance frequency according to the following equation:

$$f_1 = \frac{1}{2\pi}\sqrt{\frac{k_1}{\bar{m} + \alpha_s m_1}}$$

wherein, $f_1$ is the measured first resonance frequency of the microcantilever;
wherein, $k_1$ is a spring constant of the microcantilever;
wherein, $\bar{m}$ is a mass of the microcantilever, the substrate, and any fluid contained therein;
wherein, $\alpha_s$ is a geometric constant reflecting a distribution of the particles on the microcantilever; and
wherein, $m_1$ is the first mass of the particles.

3. The method of claim 1, wherein the second mass is determined based on the following two equations:

$$f_2^a = \frac{1}{2\pi}\sqrt{\frac{k_2}{\bar{m} + \alpha_s m_2 + \alpha_t^a m_t}}$$

$$f_2^b = \frac{1}{2\pi}\sqrt{\frac{k_2}{\bar{m} + \alpha_s m_2 + \alpha_t^b m_t}}$$

wherein, $f_2^a$ is the measured second resonance frequency of the microcantilever when the known test mass is at the first position;
wherein, $f_2^b$ is the measured second resonance frequency of the microcantilever when the known test mass is at the second position;

wherein $\alpha_t^a$ is a geometric constant reflecting the distribution of the test mass on the microcantilever at the first position;

wherein $\alpha_t^b$ is a geometric constant reflecting the distribution of the test mass on the microcantilever at the second position;

wherein $m_t$ is the known test mass;

wherein, $k_2$ is a spring constant of the microcantilever;

wherein, $\overline{m}$ is a mass of the microcantilever, the substrate, and any fluid contained therein;

wherein, $\alpha_s$ is a geometric constant reflecting a distribution of the particles on the microcantilever; and wherein, $m_2$ is the second mass of the particles.

4. The method of claim 1 wherein, measuring the first and second resonance frequencies of microcantilever further comprise:
exciting the microcantilever using an electrostatic drive electrode.

5. The method of claim 1 wherein, measuring the first and second resonance frequencies of microcantilever further comprise:
detecting the resulting resonance frequency using an optical sensor.

6. The method of claim 1 wherein, the microcantilever comprises:
a body having a free end and a fixed end;
wherein, the fixed end is connected to a rigid base;
wherein, the body is flexible.

7. The method of claim 6 wherein, the body of the microcantilever is surrounded by a vacuum.

8. The method of claim 6 wherein, the microcantilever further comprises:
a microchannel located at least partially on or within the body of the microcantilever, the microchannel configured to transport fluid to and from the substrate.

9. The method of claim 8 further comprising:
conveying food to and removing waste from the particles accumulated on the substrate of the microcantilever via the microchannel.

10. The method of claim 1 wherein, the substrate is located on or within the microcantilever; and wherein, the substrate is configured to support the accumulation, growth, or reproduction of the particles.

11. The method of claim 10 wherein, the substrate comprises a lattice, mesh, or set of linear notches within a chamber located on or within the body of the microcantilever.

12. The method of claim 1 wherein, the microcantilever is formed out of one or more silicon-on-insulator wafers.

13. The method of claim 1, wherein the microcantilever comprises:
a test mass microchannel configured to transport the known test mass in fluid between the first position and the second position using switchable flow of the fluid.

14. The method of claim 1, wherein the microcantilever comprises:
a test mass chamber configured to transport the known test mass between the first position and the second position using variable pressure.

15. The method of claim 1, wherein the microcantilever comprises:
a test mass chamber configured to transport the known test mass between the first position and the second position using switchable magnets.

16. The method of claim 1, wherein the microcantilever comprises:
a micromechanical actuator configured to transport the known test mass between the first position and the second position.

17. The method of claim 1, wherein at least one of the first position and the second position is located on or within the microcantilever.

18. A microcantilever apparatus for determining the change in mass of particles accumulated on a substrate, the microcantilever apparatus comprising:
a body having a free end and a fixed end;
wherein, the fixed end is connected to a rigid base;
wherein, the body is flexible; and
the substrate located on or within the body of the microcantilever;
wherein, the substrate is configured to support the accumulation, growth, or reproduction of the particles; and
a known test mass configured to be actuated between a first position and a second position.

19. The microcantilever apparatus of claim 18 wherein, the body of the microcantilever is surrounded by a vacuum.

20. The microcantilever apparatus of claim 18 wherein, the substrate comprises a lattice, mesh, or set of linear notches within a chamber located on or within the body of the microcantilever.

21. The microcantilever apparatus of claim 18, further comprising:
an electrostatic drive electrode configured to excite the body of the microcantilever.

22. The microcantilever apparatus of claim 18, further comprising:
an optical sensor configured to detect a resulting resonance frequency of the body of the microcantilever.

23. The microcantilever apparatus of claim 18, wherein the change in mass of the particles is performed by:
determining a first mass of the particles at a first time based on a measured first resonance frequency of the body of the microcantilever apparatus; and
determining a second mass of the particles at a second time based on a measured second resonance frequency of the body of the microcantilever apparatus, wherein determining the second mass of the particles at the second time includes:
measuring the second resonance frequency of the microcantilever when the known test mass is at a first position; and
measuring the second resonance frequency of the microcantilever when the known test mass is at the second position.

24. The microcantilever apparatus of claim 18, wherein at least one of the first position and second position is located on or within the body of the microcantilever.

25. The microcantilever apparatus of claim 18, further comprising:
a test mass microchannel located at least partially on or within the body of the microcantilever, the test mass microchannel configured to transport the known test mass in fluid between the first position and the second position using switchable flow of the fluid.

26. The microcantilever apparatus of claim 18, further comprising:
a test mass chamber located at least partially on or within the body of the microcantilever, the test mass chamber configured to transport the known test mass between the first position and the second position using variable pressure.

27. The microcantilever apparatus of claim 18, further comprising:
- a test mass chamber located at least partially on or within the body of the microcantilever, the test mass chamber configured to transport the known test mass between the first position and the second position using switchable magnets.

28. The microcantilever apparatus of claim 18, further comprising:
- a track located at least partially on or within the body of the microcantilever running from the first position to the second position; and
- a micromechanical actuator configured to transport the known test mass along the track between the first position and the second position.

29. The microcantilever apparatus of claim 18, further comprising:
- a microchannel located at least partially on or within the body of the microcantilever, the microchannel configured to transport fluid to and from the substrate.

30. The microcantilever apparatus of claim 29:
wherein, the particles are biological; and
wherein, the microchannel is configured to convey food to and waste from the particles accumulated on the substrate.

31. The microcantilever apparatus of claim 18 wherein, the microcantilever is formed out of one or more silicon-on-insulator wafers.

32. A system for determining the change in mass of accumulated particles, the system comprising:
- a means for supporting the accumulation, growth, or reproduction of the particles at an accumulation point on or within a microcantilever;
- a means for exciting the microcantilever;
- a means for measuring resulting resonance frequencies of the microcantilever in response to excitement;
- means for actuating a known test mass between a first position and a second position; and
- a means for determining the change in mass of the accumulated particles by:
  - determining a first mass of the particles at a first time based on a measured first resonance frequency of the microcantilever;
  - determining a second mass of the particles at a second time based on a measured second resonance frequency of the microcantilever, wherein determining the second mass of the particles at the second time includes:
    - measuring the second resonance frequency of the microcantilever when a known test mass is at the first position; and
    - measuring the second resonance frequency of the microcantilever when the known test mass is at the second position;
  - wherein the change in mass of the particles is based on the first mass and the second mass.

33. The system of claim 32,
wherein the first or second position is located on or within the microcantilever.

34. The system of claim 32 further comprising:
- a means for transporting food to and waste from the particles at the accumulation point.

* * * * *